United States Patent
Burke et al.

(10) Patent No.: US 6,210,683 B1
(45) Date of Patent: Apr. 3, 2001

(54) STABILIZERS CONTAINING RECOMBINANT HUMAN SERUM ALBUMIN FOR LIVE VIRUS VACCINES

(75) Inventors: Carl Burke, Pennsburg; David Volkin, Doylestown, both of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/140,428

(22) Filed: Aug. 26, 1998

Related U.S. Application Data (60) Provisional application No. 60/057,937, filed on Sep. 5, 1997.

(51) Int. Cl.$^7$ .................................................. A61K 39/25

(52) U.S. Cl. .................. 424/230.1; 435/237; 435/239; 424/212.1; 424/219.1

(58) Field of Search ............................. 424/218.1, 230.1, 424/212.1, 219.1; 435/237, 239

(56) References Cited

U.S. PATENT DOCUMENTS

| | | | |
|---|---|---|---|
| 3,783,098 | 1/1974 | Calnek et al. | 195/1.1 |
| 3,915,794 | 10/1975 | Zygraich et al. | 195/1.8 |
| 4,000,256 | 12/1976 | Hilleman et al. | 424/89 |
| 4,147,772 | 4/1979 | McAleer | 424/89 |
| 4,273,762 | 6/1981 | McAleer et al. | 424/89 |
| 4,337,242 | 6/1982 | Markus et al. | 424/89 |
| 4,338,335 | 7/1982 | McAleer et al. | 424/361 |
| 4,952,674 | 8/1990 | Keller et al. | 530/326 |
| 4,985,244 | 1/1991 | Makino et al. | 424/89 |
| 5,024,836 | 6/1991 | McAleer | 424/89 |
| 5,098,704 | 3/1992 | Valenzuela | 424/89 |
| 5,360,736 | 11/1994 | Provost et al. | 435/240.21 |
| 5,607,852 | 3/1997 | Provost et al. | 435/404 |

FOREIGN PATENT DOCUMENTS

| | | |
|---|---|---|
| 0 252 059 A2 | 1/1988 | (EP) . |
| 0 353 108 A1 | 1/1990 | (EP) . |
| 0 568 726 A2 | 11/1993 | (EP) . |
| 57-007423A | 1/1982 | (JP) . |
| WO 98/28000 | 7/1998 | (WO) . |

OTHER PUBLICATIONS

Kragh–Hansen, et al., "Molecular Aspects of Ligand Binding to Serum Albumin", Pharmacological Reviews, vol. 33, No. 1, pp. 17–53, 1981.

Burke, et al., "Formulation, Stability, and Delivery of Live Attenuated Vaccines for Human Use", Critical Reviews in Therapeutic Drug Carrier Systems, vol. 16, No. 1, pp. 1–83, 1999.

Pickart, et al., "Alteration in Biological Properties of Human Albumin During Storage", vol. 74, No. 3, pp. 961–968, 1977.

Costantino, et al., "Heterogeneity of serum albumin samples with respect to solid–state aggreation via thiol–disulfide interchange—Implications for sustained release from polymers", Journal of Controlled Release, vol. 44, pp. 255–261, 1997.

Pikal, "Freeze–Drying of Proteins Part II: Formulation Selection", BioPharm, Oct. 1990, pp. 26–30.

MacKenzie, et al., "Collapse during freeze drying—qualitative and quantitative aspects", In Freeze–Drying and Advance Food Technology, Academic Press (London), pp. 277–307, 1975.

Tarelli, et al., "Recombinant Human Albumin as a Stabilizer for Biological Materials and for the Preparation of International Reference Reagents", Biologicals, vol. 26, 1998, pp. 331–346.

Kjeldsen, et al., "Secretory Expression of Human Albumin Domains in *Saccharomyces cerevisiae* and Their Binding of Myristic Acid and an Acylated Insulin Analogue", Protein Expression and Purification, vol. 13, pp. 163–169, 1998.

Harris, et al., "Observation of Albumin Resonances in Proton Nuclear Magnetic Resonance Spectra of Human Blood Plasma: N–Terminal Assignments Aided by Use of Modified Recombinant Albumin", Analyst, Jul. 1996, vol. 121, pp. 913–922.

Twine, et al., "Characterisation of domain fragments of recombinant human albumin", Biochemical Society Transactions, vol. 26, 1988, p. S279.

Ikegaya, et al., "Complete Determination of Disulfide Forms Purified Recombinant Human Serum Albumin, Secreted by the Yeast *Pichia pastoris*". Anal. Chem., vol. 69, 1997, pp. 1986–1991.

Ohtani, et al., "Analysis of *Pichia pastoris* Components in Recombinant Human Serum Albumin by Immunological Assays and by HPLC with Pulsed Amperometric Detection", Anal. Chem., vol. 70, 1998, pp. 425–429.

Ohtani, et al., "Physicochemical and Immunochemical Properties of Recombinant Human Serum Albumin from *Pichia pastoris*", Analytical Biochemistry, vol. 256, 1998, pp. 56–62.

Fitos, et al., "Binding Studies With Recombinant Human Serum Albumin Obtained By Expression Of A Synthetic Gene In Yeast", Biochemical Pharmacology, vol. 46, No. 7, 1993, pp. 1159–1163.

Quirk, et al., "Production of Recombinant Human Serum Albumin from *Saccharomyces cerevisiae*", Biotechnology and Applied Biochemistry, vol. 11, 1989, pp. 273–287.

(List continued on next page.)

Primary Examiner—Donna C. Wortman
(74) Attorney, Agent, or Firm—Joseph A. Coppola; Jack L. Tribble (57) ABSTRACT

Compositions are provided for improving the stability of live virus vaccines containing, e.g., live varicella zoster, measles, mumps, and rubella viruses. Such improved stabilizers are aqueous solutions containing recombinant human serum albumin (rHA) as a component at from 1–100 g/l. Live virus vaccines as well as methods of preparing live virus vaccines containing the stabilizers are also provided.

19 Claims, 1 Drawing Sheet

OTHER PUBLICATIONS

Costantino, et al., "Aggregation of a Lyophilized Pharmaceutical Protein, Recombinant Human Albumin: Effect of Moisture and Stabilization by Excipients", Biotechnology, vol. 13, May 1995, pp. 493–496.

Brunell, et al., "Separation of Infectious Varicella–Zoster Virus from Human Embryonic Lung Fibroblasts", Virology, vol. 31, 1967, 732–734.

Rapp, "Inhibition by Metabolic Analogues of Plaque Formation by Herpes Zoster and Herpes Simplex Viruses", J. Immunol., vol. 93, 1964, pp. 643–648.

Plotkin, et al., "Chapter 23—Rabies Vaccine", Vaccines—Second Edition, 1994, pp. 649–670.

"Use of Recombinant Human Albumin in the Formulation of Proteins," Research Disclosure, published by Kenneth Mason Publications, Ltd. Aug. 1995, No. 376, p. 516, disclosed anonymously.

Asano, et al., "Studies on Neutralization of Varicella–Zoster Virus and Serological Follow–up of Cases of Varicella and Zoster", Biken Journal, vol. 21, pp. 15–23, 1978.

Takahashi, et al., "Development of a Live Attenuated Varicella Vaccine", Biken Journal, vol. 18, pp. 25–33, 1975.

Krah, et al., "Enhancement of varicella–zoster virus plaquing efficiency with an agarose overlay medium", J. of Virol., Methods, vol. 27, pp. 319–326, 1990.

Costantino, et al., "Aggregation of a Lyophilized Pharmaceutical Protein, Recombinant Human Albumin . . . ", Biotechnology, vol. 13, pp. 493–496, May 1995.

Day, et al., "Nonenzymatically Glucosylated Albumin", The Journal of Biological Chemistry, vol. 254, No. 3, pp. 595–597, Feb. 10, 1979.

Dodsworth, et al., "Comparative studies of recombinant human albumin and human serum albumin . . . ", Biotechnol. Appl. Biochem., vol. 24, pp. 171–176, 1996.

Bennett, et al., "The Effects of Freeze–Drying on the Potency and Stability of Live Varicella Virus Vaccine", International Symposium on Biol. Product Freeze–Drying and Formulation, Bethesda, USA, Develop. Biol. Standard, vol. 74, pp. 215–221, 1991.

Howell, et al., "Effect of Sucrose Phosphate and Sorbitol on Infectivity of Enveloped Viruses During Storage", J. of Clin. Microb., pp. 658–662, Sep. 1983.

Bovarnick, et al., "The Influence of Certain Salts, Amino Acids, Sugars, and Proteins on the Stability of Rickettsiae", J. Bact., vol. 59, pp. 509–522, 1950.

1997 Edition of the Physician's Desk Reference, pp. 1807–1910, 1997.

1997 Edition of the Physician's Desk Reference, pp. 1730–1732, 1997.

STABILIZERS CONTAINING RECOMBINANT HUMAN SERUM ALBUMIN FOR LIVE VIRUS VACCINES

CROSS-REFERENCE TO RELATED APPLICATIONS

This application claims the benefit of U.S. Provisional Application No. 60/057,937, filed Sep. 5, 1997, the contents of which are incorporated herein by reference in their entirety.

FIELD OF THE INVENTION

The present invention pertains to the use of recombinant human serum albumin in stabilizers for live virus vaccines including vaccines comprising varicella zoster, measles, mumps, and rubella viruses, individually or in combination.

BACKGROUND OF THE INVENTION

Varicella zoster virus (VZV) is a member of the herpesvirus family that causes chicken pox and zoster (shingles). Chickenpox is a highly contagious disease that occurs in persons with no antibodies or cell-mediated immunity to VZV. More than 90% of the population is exposed to VZV during the first two decades of life. In non-immunosuppressed children, chickenpox is characterized by mild to moderate fever and the development of maculopapular and vesicular lesions. These lesions appear primarily on the face and trunk and usually last from three to five days. Although generally not a serious problem in non-immunosuppressed children, VZV-caused disease is a severe threat to the immunosuppressed and to adults. In many cases, VZV becomes latent in dorsal root ganglion cells. Shingles, a painful chronic condition, occurs when VZV is reactivated from the latent state.

Measles is a negative-stranded RNA virus belonging to the genus Morbillivirus. The measles virus is highly contagious in its human host and is disseminated by coughing and sneezing from an infected host. The virus enters the bloodstream, spreads through the body and infects lymphoid tissues. A period of infectivity persists from approximately 6–7 days prior to appearance of a rash through about 2–3 days subsequent to appearance of the rash. Prodromal symptoms of fever and malaise occur about 10 days subsequent to exposure. This is followed by a hacking cough, coryza, conjunctivitis, and possibly photophobia. Koplik spots appear approximately 2 days prior to appearance of the rash. During the stage of maximal severity of the infection the patient may complain of headaches, abdominal pain, vomiting, diarrhea, and/or myalgia.

Mumps is a negative-stranded RNA virus belonging to the genus Paramyxovirus. The incubation period for the mumps virus is usually 17–21 days, but may range from 8 to 37 days. After infection and growth in the respiratory tract, the virus enters the bloodstream where it is systemically delivered to various body tissues. Mumps is characterized by swelling and tenderness of the parotid gland and occasionally other salivary glands. Prior to swelling the patient may experience pain behind the jaw and just below the ear, which is increased by pressure and movement of the jaws. More severe cases may include prodromal symptoms such as anorexia, headache, vomiting, myaglia, and high fever.

Rubella virus is a positive-stranded RNA virus which is the sole member of the family Togaviridae and which causes german measles. Rubella infection usually occurs by airborne spread of infected droplets. Many rubella infections are subclinical, with a ratio of approximately 2:1 of inapparent to overt disease. The incubation period for rubella virus is 14–21 days, with a characteristic pattern of adenopathy, rash and low grade fever. Rubella during early pregnancy frequently results in fetal infection, which may be chronic and may produce a spectrum of illness known as Congenital Rubella Syndrome (CRS).

Prevention of disease caused by varicella zoster, measles, mumps, and rubella viruses is a highly desirable goal and there are now commercially available live virus vaccines for these viruses. For example, there is now a vaccine for varicella zoster virus produced by Merck & Co., Inc. (VARIVAX®). Another vaccine produced by Merck & Co., Inc., M-M-R®II, is a live vaccine containing measles, mumps, and rubella viruses.

One difficulty in developing and using live virus vaccines such as VARIVAX® and M-M-R®II is that the viruses contained in such vaccines tend to be unstable. For example, cell-free live varicella zoster virus (VZV) is among the most labile of live viruses currently used in vaccines. The lability of VZV pertains not only to the virus as present in vaccine preparations, but also to the virus while it is being harvested from cell culture, and to the procedures used for lyophilizing the virus for long term storage (Bennett et al., 1991, Develop. Biol. Stand. 74:215–221). Because of this lability, VZV vaccines, like other live virus vaccines, must be combined with a stabilizing medium, even when lyophilized. See, e.g., U.S. Pat. Nos. 4,338,335; 4,147,772; and Howell & Miller, 1983, J. Clin. Microbiol. 18:658–662. Improvements in stabilizers for VZV are highly desirable since such improved stabilizers would permit more efficient harvesting of VZV from cell cultures as well as longer and more convenient storage of VZV vaccines. Should such improved stabilizers prove useful for other live viruses as well, they would be even more highly desirable.

Vaccine stabilizers are well known in the art as chemical compounds added to a vaccine formulation to enhance vaccine stability during low temperature storage or storage post-lyophilization.

One such chemical stabilizer is referred to as SPGA and is described in Bovarnick et al., 1950, J. Bact. 59:509–522. One liter of SPGA contains 0.218M sucrose (74.62 g), 0.00376 M $KH_2PO_4$ (0.52 g), 0.0071 M $K_2HPO_4$ (1.25 g), 0.0049 M potassium glutamate (0.912 g) and 1% serum albumin (10 g).

U.S. Pat. No. 3,783,098 discloses a modification of SPGA wherein monosodium glutamate is substituted for monopotassium glutamate. Also, use of a starch hydrosylate such as glucose or dextran maybe substituted wholly or partly for sucrose. Casein or PVP may be substituted wholly or partly for albumin as described in U.S. Pat. No. 3,915,794.

U.S. Pat. No. 4,000,256 describes an SPGA stabilizer containing, per liter of sterile distilled water: 74.62 g sucrose, 0.45 g $KH_2PO_4$, 1.35 g $K_2HPO_4$, 0.956 g monosodium L-glutamate, and 40 ml of a 25% solution of human serum albumin.

In general, an SPGA stabilizer contains from about 2 to about 10% of a particular sugar, (e.g., sucrose), from about 0.05 to about 0.3% of a mono- or dibasic alkali metal phosphate salt or mixture thereof, e.g., $KH_2PO_4$, $K_2HPO_4$, $NaH_2PO_4$, or $Na_2HPO_4$, from about 0.05 to about 0.2% of a glutamic acid alkali metal salt, e.g., sodium or potassium glutamate; and from about 0.5% to about 2% serum albumin, e.g., bovine serum albumin or human serum albumin.

Another chemical stabilizer known in the art comprises hydrolyzed gelatin, Medium O, and sorbitol. This chemical stabilizer, disclosed in U.S. Pat. No. 4,147,772, comprises approximately 3.5% hydrolyzed gelatin, 3.5% sorbitol, and 1.0% Medium O, along with minimal amounts of sodium bicarbonate and phenol red.

A vaccine stabilizer modified from U.S. Pat. No. 4,147,772 is disclosed in U.S. Pat. No. 4,273,762. This stabilizer comprises the components disclosed in U.S. Pat. No. 4,147,772 as well as minute amounts of DPG solution, which contains, among other compounds, cysteine, glutathionine, ascorbic acid, and vitamin A.

Stabilizers for live virus vaccines generally require high concentrations of sugars such as sucrose, mannitol, or sorbitol to improve virus stability during lyophilization and storage. In addition, the virus bulks contain relatively high concentrations of salts in the tissue culture media. Such high concentrations of sugars and salts make freeze drying of the vaccine preparations difficult. One problem is that physical collapse of the vaccine preparation may occur upon freeze drying. Polymer additives such as dextran, non-recombinant human serum albumin (HSA), as well as nonhydrolyzed and hydrolyzed gelatin have been added to vaccines to raise the collapse temperature. In the case of HSA and gelatin, the inclusion of these materials may raise potential safety concerns if these materials are derived from at-risk human or animal sources. These additives do not necessarily solely stabilize the virus against inactivation; they also help to prevent the physical collapse of the freeze-dried material during lyophilization and subsequent storage in the solid state. Thus, it would be advantageous to develop stabilizers which both directly stabilize the live virus against inactivation, as well as protect against physical collapse of the vaccine preparation in the lyophilized state.

SUMMARY OF THE INVENTION

The present invention provides compositions for improving the stability of live virus vaccines containing live viruses such as, e.g., live varicella zoster, measles, mumps, and rubella viruses. Such improved stabilizers contain recombinant human serum albumin (rHA) as a component. The inclusion of rHA in such compositions results in improved stability of the vaccines in both the liquid and solid state as well as improved yields during the process of harvesting virus for vaccine preparation. The use of rHA allows for the formulation of vaccine stabilizers that do not contain products of animal origin, e.g., non-recombinant human serum albumin or gelatin.

The improved stabilizers containing rHA can be used to prepare vaccines that contain varicella zoster virus, measles, mumps, and rubella viruses, where these viruses are present in the vaccine either individually or in combination. Accordingly, the present invention also provides vaccines comprising varicella zoster virus, measles, mumps, and rubella viruses, individually, or in combination, where the vaccine contains rHA.

Methods of preparing vaccines containing a live virus and rHA are also provided.

DETAILED DESCRIPTION OF THE INVENTION

The present invention is directed to compositions that are improved stabilizers for live virus vaccines. The improved stabilizers replace components of previous stabilizers such as non-hydrolyzed or hydrolyzed gelatin and non-recombinant human serum albumin (HSA) with recombinant human serum albumin (rHA). The present invention also provides vaccines comprising such improved stabilizers.

The present invention represents a significant improvement over the use of prior art stabilizers that included such components as gelatin or HSA in that rHA has been found to stabilize live viruses against inactivation (when compared to hydrolyzed gelatin) as well as to afford increased protection against the collapse of lyophilized vaccines.

That rHA could be substituted for HSA was not expected in that there are significant chemical differences between rHA and HSA. For example, rHA does not possess the chemical heterogeneity that is found in HSA purified from serum with respect to glycation, lipid content, and bound ligands (see, e.g., Day et al., 1979, J. Biol. Chem. 254: 595–597). HSA preparations also contain albumin dimers and higher order oligomers which are only present at low levels in rHA (see, e.g., Dodsworth et al., 1996, Biotechnol. Appl. Biochem. 24: 171–176). Thus, rHA is a very different and much more well-defined protein than HSA. In addition, the well-known problems associated with aggregation of rHA in the lyophilized state had to be overcome before rHA could be incorporated in vaccine stabilizers (see, e.g., Constantino et al., 1995, Bio/Technol. 13:493–496).

The present invention includes compositions for stabilizing live virus vaccines including varicella zoster virus (VZV), measles, mumps, and rubella viruses wherein the compositions comprise an aqueous solution of from 0.1% to 10%, preferably from 0.5% to 5.0%, and even more preferably, from 1.0% to 3.0%, of recombinant human serum albumin (rHA) (w/v). In a particular preferred embodiment, the composition comprises 2.5% rHA (w/v). In a particular embodiment, the compositions do not contain gelatin or HSA.

In a particular embodiment, the composition per liter of solution is:

| | |
|---|---|
| rHA | 25 g |
| Potassium Chloride | 0.16 g |
| Potassium Phosphate Monobasic | 0.16 g |
| Sodium Chloride | 6.4 g |
| Sodium PhosphateDibasic | 0.91 g |
| Sodium L-glutamate | 1.0 g |
| Sucrose | 50.0 g |
| Water | balance |

The pH is adjusted to pH 7.0 with NaOH.

The rHA can be conveniently provided by employing an rHA solution such as, e.g., 100 ml of a 25% (w/v) rHA solution. "rHA solution" refers to an aqueous solution of rHA that can also contain 0.16 mmol of octanoate per gram of rHA and 15 mg of TWEEN®80 per liter.

It will be recognized by those of skill in the art that the composition of each of the components of the above solution can be varied somewhat. For example: the sucrose composition can be from about 20–90 g/l; the phosphate can be provided not only as potassium phosphate monobasic and sodium phosphate dibasic, but also as any mono- or dibasic alkali metal phosphate salt or mixture thereof, e.g., $KH_2PO_4$, $K_2HPO_4$, $NaH_2PO_4$, or $Na_2HPO_4$, at a total phosphate concentration of from about 0.5–3 g/l; the L-glutamate can be provided by any glutamic acid alkali metal salt, e.g., sodium or potassium glutamate, at about 0.5–2 g/l; the chloride concentration can be varied somewhat, and can be provided as various combinations of sodium chloride or potassium chloride. Of course, as discussed above, the rHA concentration can vary as well. Also, the sucrose listed in the above-described stabilizer can be substituted with other sugars and sugar alcohols such as lactose, glucose, fructose, sorbitol, or mannitol.

Accordingly, the present invention includes stabilizers comprising from 1–100 g/l, preferably from 5–50 g/l, and even more preferably, from 10–30 g/l, of recombinant human serum albumin (rHA); a sugar or sugar alcohol such as sucrose, sorbitol, lactose, glucose, fructose, or mannitol at 20–90 g/l; a mono- or dibasic alkali metal phosphate salt or mixture thereof, e.g., $KH_2PO_4$, $K_2HPO_4$, $NaH_2PO_4$, or $Na_2HPO_4$, at a total phosphate concentration of 0.5–3 g/l; a glutamic acid alkali metal salt, e.g., sodium or potassium glutamate, at 0.5–2 g/l; and a combination of sodium and potassium chloride providing a total chloride concentration of 4–10 g/l.

In a particular embodiment, the present invention includes stabilizers containing, per liter of solution:

| | |
|---|---:|
| rHA | 5–50 g |
| Potassium Chloride | 0.05–0.3 g |
| Potassium Phosphate Monobasic | 0.05–0.3 g |
| Sodium Chloride | 4–10 g |
| Sodium PhosphateDibasic | 0.5–2 g |
| Sodium L-glutamate or Potassium L-glutamate | 0.5–2 g |
| Sucrose, Sorbitol, Lactose, Glucose, Fructose, or Mannitol | 20–90 g |
| Water | balance |

The pH is adjusted to pH 7.0 with NaOH.

In related embodiments, the stabilizers described above can also contain EDTA at 0.1–2 g/l. For example, the present invention also includes the following composition, per liter:

| | |
|---|---:|
| rHA | 25 g |
| Potassium Chloride | 0.16 g |
| Potassium Phosphate Monobasic | 0.16 g |
| Sodium Chloride | 8.0 g |
| Sodium PhosphateDibasic | 1.15 g |
| Sucrose | 50.0 g |
| EDTA Trisodium Salt | 0.3 g |
| Water | balance |

The pH is adjusted to pH 7.0 with NaOH.

In another embodiment, the present invention includes a stabilizer wherein the composition per liter of solution is:

| | |
|---|---:|
| rHA | 26.75 g |
| Sorbitol | 56.8 g |
| 1M Sodium Phosphate, pH 6.2 | 75.0 ml |
| Tissue Culture Medium | balance |

The pH is controlled by the phophate buffer, resulting in a final pH of 6.5–6.8.

"Tissue Culture Medium" can contain amino acids, vitamins, inorganic salts, as well as other components. Various media can be used, such as Medium 199 or Minimum Essential Medium (Gibco/Life Technologies catalog, 1997, p. 1–53). Tissue culture medium may also contain small amounts of sodium bicarbonate, neomycin, or other components used for maintaining cell growth and integrity.

In the stabilizer described immediately above, the rHA concentration can be varied from 1–100 g/l, is preferably from 5–50 g/l, and is even more preferably from 10–30 g/l. The sorbitol can be present in the range of 20–90 g/l. Sucrose is optionally present at up to 70 g/l.

In another embodiment, the present invention provides a stabilizer whose composition per liter of solution is:

Medium 199 containing:

rHA at a concentration of 0.1% to 10%;

50 µg/ml neomycin;

2 mM L-glutamine and;

25% SPG;

where SPG is SPGA (described below) without albumin.

In a particular embodiment of the stabilizer described immediately above, the rHA is present at a concentration of 0.5% to 5%; in another embodiment, the rHA is present at a concentration of 1% to 3%.

The present invention includes stabilizers formed by the substitution of rHA for the HSA, bovine serum albumin, or gelatin found in many prior art stabilizers. For example, U.S. Pat. No. 4,338,335 discloses a stabilizer containing, on a weight/volume basis, in sterile distilled water:

from about 2% to 10% sugar, e.g., sucrose;

from about 0.05% to 0.3% of a mono- or dibasic alkali metal phosphate salt or mixture thereof, e.g., $KH_2PO_4$, $K_2HPO_4$, $NaH_2PO_4$, or $Na_2HPO_4$;

from about 0.05% to 0.2% of a glutamic acid alkali metal salt, e.g., sodium or potassium glutamate; and from about 0.5% to 2% bovine serum albumin or HSA.

Accordingly, the present invention provides a stabilizer for live viruses that contains, on a weight/volume basis, in sterile distilled water:

from about 2% to 10% sugar, e.g., sucrose;

from about 0.05% to 0.3% of a mono- or dibasic alkali metal phosphate salt or mixture thereof, e.g., $KH_2PO_4$, $K_2HPO_4$, $NaH_2PO_4$, or $Na_2HPO_4$;

from about 0.05% to 0.2% of a glutamic acid alkali metal salt, e.g., sodium or potassium glutamate; and from about 0.5% to 2% rHA.

rHA can be used to replace the polymers, HSA, or gelatin in many live virus vaccines and stabilizers described in the prior art. For example, rHA can replace casein hydrolysate and dextran in formulations described in European Patent Application EP 252059; rHA can replace HSA in formulations described in European Patent Application EP 353108; rHA can replace gelatin in formulations described in U.S. Pat. No. 4,985,244; rHA can replace casein or PVP in formulations described in U.S. Pat. No. 3,915,794.

Bovarnick et al., 1950, J. Bact. 59:509–522 described a stabilizer known as SPGA that contained, on a per liter basis:

| | |
|---|---:|
| Sucrose | 74.62 g |
| $KH_2PO_4$ | 0.52 g |
| $K_2HPO_4$ | 1.25 g |
| Potassium L-glutamate | 0.912 g |
| Bovine serum albumin | 10 g. |

Accordingly, the present invention provides a stabilizer for live viruses that contains, on a per liter basis:

| | |
|---|---|
| Sucrose | 74.62 g |
| $KH_2PO_4$ | 0.52 g |
| $K_2HPO_4$ | 1.25 g |
| Potassium L-glutamate | 0.912 g |
| rHA | 10 g. |

Sodium L-glutamate can be substituted for potassium L-glutamate in the above-described stabilizer. Also, a starch hydrosylate such as glucose or dextran can be substituted, wholly or partially, for sucrose.

U.S. Pat. No. 4,000,256 described a stabilizer that is a variant of SPGA that contained, on a per liter basis:

| | |
|---|---|
| Sucrose | 74.62 g |
| $KH_2PO_4$ | 0.45 g |
| $K_2HPO_4$ | 1.35 g |
| Monosodium L-glutamate | 0.956 g |
| HSA | 10 g. |

Accordingly, the present invention provides a stabilizer for live viruses that contains, on a per liter basis:

| | |
|---|---|
| Sucrose | 74.62 g |
| $KH_2PO_4$ | 0.45 g |
| $K_2HPO_4$ | 1.35 g |
| Monosodium L-glutamate | 0.956 g |
| rHA | 10 g. |

Another chemical stabilizer known in the art comprises hydrolyzed gelatin, Medium O, and sorbitol. This chemical stabilizer, disclosed in U.S. Pat. No. 4,147,772, comprises approximately 3.5% hydrolyzed gelatin, 3.5% sorbitol, and 1.0% Medium O, along with minimal amounts of sodium bicarbonate and phenol red. Accoding to the present invention, 3.5% rHA can be substituted for 3.5% hydrolyzed gelatin in this stabilizer to form an improved stabilizer.

A vaccine stabilizer modified from U.S. Pat. No. 4,147,772 is disclosed in U.S. Pat. No. 4,273,762. This stabilizer comprises the components disclosed in U.S. Pat. No. 4,147,772 as well as minute amounts of DPG solution, which contains, among other compounds, cysteine, glutathionine, ascorbic acid, and vitamin A. The stabilizer disclosed in U.S. Pat. No. 4,273,762 can also be improved by the substitution of rHA for hydrolyzed gelatin.

The present invention includes stabilizers formed by the substitution of rHA for the HSA or hydrolyzed gelatin found in the stabilizers described in provisional U.S. Patent Application Ser. No. 60/033,565. Accordingly, the present invention includes a stabilizer that contains from about 15 to about 90 grams per liter of a 6-carbon polyhydric alcohol, including but not limited to sorbitol, mannitol and dulcitol; from about 10 to about 70 grams per liter of a disaccharide, including but not limited to sucrose, lactose, maltose or trehalose; from about 1–100 g/l, preferably 5–50 g/l, and even more preferably 10–30 g/l, of rHA; and an amount of a physiologically active buffer to adjust the pH to between 6.0 and 7.0.

In a particular embodiment, the above-described stabilizer contains sorbitol as the 6-carbon polyhydric alcohol, from about 15 to about 90 grams per liter, and the disaccharide sucrose, from about 10 to about 70 grams per liter.

In another embodiment, the above-described stabilizer includes sodium chloride to about 10 g/l and preferably from about 1 to about 6 grams per liter; sodium bicarbonate in amounts to about 1.5 g/l, preferably from about 0.2 g/l to about 1.2 g/l; and cell culture medium which is a nutrient medium which promotes cell growth in vitro, including but not limited to known cell culture media such as Solution 199, Medium T, Medium O, Dubecco's Modified Eagles Medium, Minimal Essential Medium, and Basal Medium Eagle. Preferred media components include biologically effective amounts of Medium O, Medium T, and Solution 199. Other components of the above-described stabilizer may include, but are not limited to, biologically active amounts of an antibiotic (e.g., neomycin) and a pH indicator (e.g., phenol red).

The present invention also includes stabilizers S1 through S12 having the compositions shown in Table 1, on a g/l basis.

TABLE 1

| | rHA | Sorbitol | NaCl | Sucrose | Bicarbon-ate | Glucose | Citrate |
|---|---|---|---|---|---|---|---|
| S1 | 26.8 | 46.8 | 3.38 | 40.00 | 0 | 0.46 | 2.53 |
| S2 | 26.8 | 46.8 | 3.38 | 40.00 | 0 | 0.46 | 0 |
| S3 | 26.8 | 46.8 | 0 | 40.00 | 0 | 0 | 2.53 |
| S4 | 26.8 | 46.8 | 0 | 40.00 | 0 | 0 | 0 |
| S5 | 26.8 | 46.8 | 3.38 | 20.00 | 0 | 0.46 | 2.53 |
| S6 | 26.8 | 46.8 | 0 | 20.00 | 0 | 0 | 2.53 |
| S7 | 26.8 | 56.8 | 0 | 30.00 | 0 | 0 | 0 |
| S8 | 26.8 | 56.8 | 3.38 | 30.00 | 0 | 0.46 | 0 |
| S9 | 26.8 | 46.8 | 3.38 | 40.00 | 0.59 | 0.46 | 0 |
| S10 10 | 26.8 | 46.8 | 0 | 0 | 0 | 0 | 2.53 |
| S11 11 | 26.8 | 46.8 | 3.38 | 40.00 | 0.59 | 0.46 | 2.53 |
| S12 | 26.8 | 56.8 | 3.38 | 30.00 | 0.59 | 0.46 | 0 |

In the stabilizers listed in Table 1, the bicarbonate and citrate can be provided in any convenient form.

The present invention includes vaccines comprising a live virus, e.g., varicella zoster virus (VZV), measles virus, mumps virus, or rubella virus, individually or in combination with one or more other live viruses, in any of the above-described stabilizers of the present invention. In a particular embodiment, the vaccine contains a live virus selected from the group consisting of VZV, measles, mumps, and rubella. In another embodiment, the vaccine comprises measles, mumps, and rubella viruses. In another embodiment, the vaccine comprises VZV, measles, mumps, and rubella viruses. Other viruses may also be used with the stabilizers of the present invention. Thus, the present invention includes vaccines comprising influenza, polio, hepatitis, herpes simplex 1, or herpes simplex 2 viruses, rotavirus, or combinations thereof, in any of the above-described stabilizers of the present invention.

The concentration of rHA in the vaccine can be from 0.1% to 10%, is preferably from 0.5% to 5.0%, and, even more preferably, from 1.0% to 3.0% (w/v). In a particular preferred embodiment, the vaccine comprises 2.5% rHA (w/v). In a particular embodiment, the vaccine does not contain gelatin or HSA. Accordingly, in a particular embodiment, the present invention provides a vaccine comprising at least one live virus selected from the group consisting of VZV, measles, mumps, and rubella wherein the vaccine further comprises rHA at 0.1% to 10% (w/v). In another embodiment, the present invention provides a vaccine comprising at least one live virus selected from the group consisting of VZV, measles, mumps, and rubella wherein the vaccine further comprises rHA at 0.5% to 5% (w/v). In another embodiment, the present invention provides a vaccine comprising at least one live virus selected from the group consisting of VZV, measles, mumps, and rubella wherein the vaccine further comprises rHA at 1.0% to 3.0% (w/v). In another embodiment, the present invention provides a vaccine comprising at least one live virus selected from the group consisting of VZV, measles, mumps, and rubella wherein the vaccine further comprises rHA at 2.5% (w/v).

The present invention also includes vaccines comprising at least one virus selected from the group consisting of varicella zoster virus, measles virus, mumps virus and rubella virus; recombinant human serum albumin at a concentration of from 1–100 g/l, preferably 5–50 g/l, even more preferably 10–30 g/l, and most preferably 25 g/l; and a sugar or sugar alcohol at 20–90 g/l; a mono- or dibasic alkali metal phosphate salt or mixture thereof at a total phosphate concentration of from 0.5 to 3 g/l; a glutamic acid alkali metal salt at 0.5 to 2 g/l; and a combination of sodium and potassium chloride providing a total chloride concentration of 4–10 g/l.

The present invention also includes vaccines comprising at least one virus selected from the group consisting of varicella zoster virus, measles virus, mumps virus and rubella virus; recombinant human serum albumin at a concentration of from 1–100 g/l, preferably 5–50 g/l, even more preferably 10–30 g/l, and most preferably 25 g/l; where the vaccine further comprises, per liter:

| | |
|---|---|
| Potassium Chloride | 0.05–0.3 g |
| Potassium Phosphate Monobasic | 0.05–0.3 g |
| Sodium Chloride | 4–10 g |
| Sodium PhosphateDibasic | 0.5–2 g |
| Sodium L-glutamate or Potassium L-glutamate | 0.5–2 g |
| Sucrose, Sorbitol, Lactose, Glucose, Fructose, or Mannitol | 20–90 g. |

The present invention also includes vaccines comprising at least one virus selected from the group consisting of varicella zoster virus, measles virus, mumps virus, and rubella virus; recombinant human serum albumin at a concentration of from 1–100 g/l, preferably 5–50 g/l, even more preferably 10–30 g/l, and most preferably 25 g/l; where the vaccine further comprises, on a per liter basis:

| | |
|---|---|
| Potassium Chloride | 0.16 g |
| Potassium Phosphate Monobasic | 0.16 g |
| Sodium Chloride | 6.4 g |
| Sodium PhosphateDibasic | 0.91 g |
| Sodium L-glutamate | 1.0 g |
| Sucrose | 50.0 g. |

The present invention also includes vaccines comprising at least one virus selected from the group consisting of varicella zoster virus, measles virus, mumps virus, and rubella virus; recombinant human serum albumin at a concentration of from 1–100 g/l, preferably 5–50 g/l, even more preferably 10–30 g/l, and most preferably 25 g/l; where the vaccine further comprises, on a per liter basis: sorbitol at 20–90 g/l; sucrose at 0–70 g/l; 1 M Sodium Phosphate, pH 6.2, at 65–85 ml; and Tissue Culture Medium.

The present invention also includes vaccines comprising at least one virus selected from the group consisting of varicella zoster virus, measles virus, mumps virus, and rubella virus; recombinant human serum albumin at a concentration of from 1–100 g/l, preferably 5–50 g/l, even more preferably 10–30 g/l, and most preferably 25 g/l; where the vaccine further comprises, on a per liter basis:

| | |
|---|---|
| Sorbitol | 56.8 g |
| 1M Sodium Phosphate, pH 6.2 | 75.0 ml |
| Tissue Culture Medium | balance. |

The above-described vaccines can be lyophilized by procedures well known in the art to provide a lyophilized vaccine having improved stability.

The present invention also includes live virus vaccines in which the virus is originally not present in one of the stabilizers of the present invention but is then mixed with one of the stabilizers of the present invention in order to prepare the final vaccine formulation. The ratio (on a volume/volume basis) of virus preparation to stabilizer that is mixed to prepare the final vaccine formulation is generally from about 1:100 to 1:1. Preferably the ratio is 1:20, even more preferably 1:10, and most preferably 1:3, although ratios of 1:2 or even 1:1 are also contemplated. Thus, whatever the solution a live virus stock is present in, that stock can be mixed advantageously with one of the stabilizers of the present invention, according to the ratios above, to produce a vaccine preparation.

Accordingly, the present invention includes live virus vaccines and methods of preparation of live virus vaccines where the vaccine is prepared by mixing a live virus preparation with a stabilizer wherein the stabilizer comprises rHA at from 0.1% to 10% (w/v) of the stabilizer and the virus and stabilizer are mixed in a ratio of from about 1:100 to 1:1, with preferred ratios being 1:20, or 1:10, or 1:3.

In a particular embodiment, the stabilizer does not contain HSA or gelatin, either non-hydrolized or hydrolized.

In a particular embodiment, the live virus is selected from the group consisting of VZV, measles, mumps, and rubella.

In a particular embodiment, the stabilizer comprises rHA at from 0.5% to 5% (w/v). In another embodiment, the stabilizer comprises rHA at from 1% to 3% (w/v). In another embodiment, the stabilizer comprises rHA at 2.5% (w/v).

Following mixing of a virus preparation and a stabilizer of the present invention, as described above, the vaccine thereby formed can be lyophilized by procedures well known in the art to provide a lyophilized vaccine having improved stability.

VZV can be isolated from the papular eruptions of children in the acute phase of chickenpox. VZV isolated in this manner is cultured in vitro over multiple passages in appropriate cell lines to produce a live, attenuated virus, harvested from the cells, and used to form vaccines. This can be accomplished according to the methods described in, e.g., U.S. Pat. Nos. 4,000,256; 4,952,674; 5,360,736. Methods of combining VZV with other viruses to form multivalent vaccines are known in the art. See, e.g., U.S. Pat. No. 5,024,836 which discloses a quadrivalent vaccine of VZV, measles, mumps, and rubella. Included in the present invention is the use of rHA instead of HSA, bovine serum albumin, or gelatin in the stabilizers of the above-cited prior art methods of harvesting VZV from cell lines and making VZV vaccines. In particular, as described in detail herein, the present invention includes the use of rHA in stabilizers that are used to harvest VZV from MRC-5 cells.

Methods of measuring the titers of VZV preparations are well known in the art. See, e.g., Krah et al., 1990, J. Virol. Methods 27:319–326, which describes a method that involves culturing MRC-5 cells, which are susceptible to VZV infection, to an actively replicating state, that is, to a point where the cells are about 50–80% confluent. VZV is then overlaid onto the cell monolayer in a minimal volume, allowed to attach to the cells and then additional growth medium is added. After several days of growth, the cells are exposed to a protein stain and clear areas, or plaques, are counted.

As is the case for VZV, methods of isolating and measuring the titers of measles, mumps, and rubella viruses are well known in the art. "Hydrolyzed gelatin" refers to gelatin that has been subjected to partial hydrolysis to yield a partially hydrolyzed gelatin having a molecular weight of about 3,000. This gelatin hydrolysis product has approximately the same amino acid composition as gelatin. Unlike gelatin which forms gels but is insoluble in cold water, hydrolyzed gelatin does not gel but is soluble in cold water and other common liquids such as milk and orange juice. Aqueous solutions containing up to about 10% hydrolyzed gelatin do not increase appreciably in viscosity. Above about 10% concentration, viscosity increases slowly. At about 50% concentration, solutions are quite viscous. The typical amino acid composition of hydrolyzed gelatin is known. Partially hydrolyzed gelatin may be obtained from any number of commercial sources, for instance under the tradename Dynagel. Partially hydrolyzed gelatin may also be obtained by enzymatic hydrolysis of gelatin by means of a proteolytic enzyme, such as, for example, papain, chymopapain, and bromelin, although other known hydrolysis means may be employed, e.g., acid hydrolysis. "MEM" is a tissue culture medium that is described in the Gibco/Life Technologies Catalog, 1997, p. 1–57.

The following non-limiting examples are presented to better illustrate the invention.

EXAMPLE 1

Recombinant Human Serum Albumin Stabilizes Varicella Zoster Virus Alone or in Combination with Other Viruses at Many Temperatures Over Various Periods of Time.

Stability at 4° C.

The stability of varicella zoster virus (VZV) alone (VARIVAX®) or in combination with measles, mumps, and rubella live viruses (M-M-R®II-VZV) at 4° C. was tested in stabilizers with and without recombinant human serum albumin (rHA). VARIVAX® is a currently licensed VZV vaccine that is described at pages 1807–1810 of the 1997 edition of the Physician's Desk Reference (Medical Economics, Montvale, N.J.). M-M-R®II-VZV is a quadrivalent vaccine currently under development by Merck & Co., Inc. that includes VZV in PGS stabilizer (see below) and M-M-R®II. M-M-R®II is a live vaccine containing measles, mumps, and rubella viruses that is described on pages 1730–1732 of the 1997 edition of the Physician's Desk Reference (Medical Economics, Montvale, N.J.).

The stabilizer PGS with EDTA is known in the art and has been described in various publications (e.g., Koyama, K., and Osame, J., Stabilized live vaccine, EP patent 568726 A2, 1993).

PGS contains the following ingredients on a per liter basis:

| Hydrolyzed Gelatin | 25 g |
|---|---|
| Potassium Chloride | 0.16 g |
| Potassium Phosphate Monobasic | 0.16 g |
| Sodium Chloride | 6.4 g |
| Sodium PhosphateDibasic | 0.91 g |

-continued

| Sodium L-glutamate | 1.0 g |
|---|---|
| Sucrose | 50.0 g |
| Water | balance. |

As a stabilizer containing rHA, the hydrolyzed gelatin of PGS was replaced by an equivalent weight of rHA to form the stabilizer P(rHA)S. Thus, the composition of P(rHA)S on a per liter basis is:

| rHA Solution, 25% w/v | 100 mL |
|---|---|
| Potassium Chloride | 0.16 g |
| Potassium Phosphate Monobasic | 0.16 g |
| Sodium Chloride | 6.4 g |
| Sodium PhosphateDibasic | 0.91 g |
| Sodium L-glutamate | 1.0 g |
| Sucrose | 50.0 g |
| Water | balance. |

The concentration of rHA in P(rHA)S is 2.5% (w/v), or 25 g/l.

VZV infected MRC-5 cells were harvested, sonicated, and clarified in both stabilizers (PGS and P(rHA)S) and then lyophilized, either alone as in VARIVAX®, or in combination with measles, mumps, and rubella viruses, as MMRII®-VZV. The lyophilized viral preparations were then incubated at 4° C. for three months.

Following these incubations, VZV viral titers were measured as described in Krah et al., 1990, J. Virol. Methods 27:319. The results are shown in Table 2 and are reported as percent PFU/ml remaining at the indicated time. Table 2 shows that the inclusion of rHA rather than gelatin in the stabilizer resulted in equivalent or increased potency of the virus after incubation at 4° C. for two and three months.

TABLE 2

| Time in 4° C. incubation | VZV Potency % remaining - VZV in P(rHA)S | VZV Potency % remaining - MMRII ®-VZV in P(rHA)S | VZV Potency % remaining - VZV in PGS |
|---|---|---|---|
| 1 month | 77 | 78 | 84 |
| 2 months | 86 | 72 | 68 |
| 3 months | 65 | 61 | 61 |

Stability at 30° C.

The stability of lyophilized VZV alone (VARIVAX®) or lyophilzed in combination with measles, mumps, and rubella live viruses (M-M-R®II-VZV) at 30° C. was tested in stabilizers with and without rHA. As a stabilizer without rHA, PGSE was used. PGSE contains the following amounts per liter:

| Hydrolyzed Gelatin | 25.0 g |
|---|---|
| Potassium Chloride | 0.16 g |
| Potassium Phosphate Monobasic | 0.16 g |
| Sodium Chloride | 8.0 g |
| Sodium PhosphateDibasic | 1.15 g |
| Sucrose | 50 g |
| EDTA Trisodium Salt | 0.3 g |
| Water | balance. |

As a stabilizer containing rHA, the hydrolyzed gelatin of PGSE was replaced by an equivalent weight of rHA to form the stabilizer P(rHA)SE. Thus, the composition of P(rHA)SE on a per liter basis is:

| | |
|---|---|
| rHA Solution, 25% (w/v) | 100 mL |
| Potassium Chloride | 0.16 g |
| Potassium Phosphate Monobasic | 0.16 g |
| Sodium Chloride | 8.0 g |
| Sodium PhosphateDibasic | 1.15 g |
| Sucrose | 50.0 g |
| EDTA Trisodium Salt | 0.3 g |
| Water | balance. |

The concentration of rHA in P(rHA)SE is 2.5% (w/v), or 25 g/l.

In a manner similar to that described above for the stability tests done at 4° C., VZV, either alone as VARIVAX®, or in combination with measles, mumps, and rubella viruses, as M-M-R®II-VZV, was incubated at 30° C. for one week in either PGSE or P(rHA)SE. VZV alone was also incubated at 30° C. for one week in either PGS or P(rHA)S.

Following these incubations, viral titers were measured as above. The results are shown in Table 3. Data are presented as percent of VZV PFU/ml remaining after one week at 30° C. Table 3 shows that, in all cases tested, the inclusion of rHA rather than gelatin in the stabilizer resulted in increased potency of the virus after incubation at 30° C. for one week.

TABLE 3

| Stabilizer | VZV alone | VZV in M-M-R ®II-VZV |
|---|---|---|
| PGS | 35 | — |
| P(rHA)S | 43 | — |
| PGSE | 27 | 15 |
| P(rHA)SE | 36 | 37 |

Stability at 37° C.

The stability of lyophilized VZV (as VARIVAX®) at 37° C. was tested in stabilizers with and without rHA. As a stabilizer without rHA, PGS was used. PGS is described above. As a stabilizer containing rHA, P(RHA)S was used. P(rHA)S is described above.

In a manner similar to that described above for the stability tests done at 4° C. and 30° C., VZV was incubated at 37° C. for one week in either PGS or P(rHA)S.

Following this incubation, viral titer was measured as above. The results are shown in Table 4. Data are presented as percent of VZV PFU/ml remaining after one week at 37° C. Table 4 shows that the inclusion of rHA rather than gelatin in the stabilizer resulted in increased potency of the virus after incubation at 37° C. for one week.

TABLE 4

| Stabilizer | VZV % potency remaining |
|---|---|
| PGS | 18 |
| P(rHA)S | 35 |

The results reported in this Example provide evidence for a direct affect of rHA on viral stability in the solid state during storage when compared to hydrolyzed gelatin (i.e., not an effect mediated by prevention of physical collapse of lyophilized virus plugs since neither type of formulations (with gelatin or with rHA) led to plug collapse during storage).

EXAMPLE 2
Recombinant Human Serum Albumin Stabilizes Varicella Zoster Virus During Harvesting of the Virus Varicella zoster virus (VZV) was grown in MRC-5 cells and harvested according to the procedures described in Asano & Takahashi, 1978, Biken J. 21: 15–23 and Takahashi et al., 1975, Biken J. 18: 25–33. Similar procedures are described in U.S. Pat. Nos. 5,607,852 and 5,360,736. The aforementioned procedures were modified so that the stabilizer added during harvesting was one of the three stabilizers PGS, PGF, or P(rHA)S. PGS and P(rHA)S are described above. PGF contains the following amounts on a per liter basis:

| | |
|---|---|
| Hydrolyzed Gelatin | 25 g |
| Potassium Chlorie | 0.16 g |
| Potassium Phosphate Monobasic | 0.16 g |
| Sodium Chloride | 6.4 g |
| Sodium PhosphateDibasic | 0.91 g |
| Sodium L-glutamate | 1.0 g |
| Fructose | 50.0 g |
| Water | balance. |

The same lot of virus-infected cells was used for all three stabilizers. Following harvesting, sonication, and clarification, VZV titers were determined as described above. The results are shown in Table 5.

TABLE 5

| Stabilizer | VZV titer (PFU/ml) |
|---|---|
| PGS | 100,000 |
| PGF | 142,000 |
| P(rHA)S | 1,360,000 |

Table 5 shows that the use of a stabilizer that contains rHA led to an almost ten-fold higher titer than the use of any other stabilizer. This result is evidence for increased yields during the harvesting, processing, and filtration steps. One explanation for this increased bulk potency is a direct affect of rHA on viral stability in the liquid state during processing, (i.e., not an effect mediated by prevention of physical collapse of lyophilized vaccine plugs) since no freezing or freeze-drying was involved. Another explanation is that rHA is preventing losses in viral potency during the filtration step by affecting viral bulk characteristics and virus interactions with the filtration material. Thus, the use of rHA rather than hydrolyzed gelatin confers the unexpected benefit of direct stabilization of the virus in the liquid and solid state instead of simply protection against physical collapse of lyophilized virus plugs in the solid state during storage.

EXAMPLE 3
Effect of Recombinant Human Serum Albumin on the Stability of Other Viruses The effect of recombinant human serum albumin (rHA) on the stability of other, i.e., non-varicella zoster, viruses was tested. The stability of measles, mumps, and rubella viruses was evaluated in stabilizers with and without rHA. Measles, mumps, and rubella viruses were tested as the vaccine M-M-R®II. M-M-R®II is described at pages 1730–1732 of the 1997 edition of the Physician's Desk Reference (Medical Economics, Montvale, N.J.).

As a stabilizer without rHA, GOS was used. GOS is the stabilizer in which M-M-R®II is provided. In the final M-M-R®II vaccine, GOS comprises 67.5% of the total volume and is combined with 7.5% 1 M sodium phosphate buffer, pH 6.2, and 25% viral bulks and diluents. GOS contains the following amounts in one liter of solution:

| | |
|---|---|
| Hydrolyzed Gelatin | 39.7 g |
| Sorbitol | 39.7 g |
| Tissue Culture Medium | balance. |

As a stabilizer containing rHA, the hydrolyzed gelatin of GOS was replaced by an equivalent weight of rHA to form the stabilizer (rHA)OS. Thus, the composition of (rHA)OS per liter is:

| | |
|---|---|
| rHA | 39.7 g |
| Sorbitol | 39.7 g |
| Tissue Culture Medium | balance. |

M-M-R®II was prepared with either GOS or (rHA)OS as stabilizer, lyophilized, and then incubated at 37° C. for one week. Following these incubations, viral titers were measured. The results are shown in Table 6. Data are presented as the loss in potency (expressed as log PFU/ml) after one week at 37° C.

TABLE 6

| Virus | (rHA)OS | GOS |
|---|---|---|
| Measles | 0.9 | 0.9 |
| Mumps | 1.0 | 0.9 |
| Rubella | 0.4 | 0.3 |

The results shown in Table 6 indicate that the stabilities of measles, mumps, and rubella viruses are similar in GOS and (rHA)OS. These results demonstrate that the inclusion of rHA in stabilizers does not adversely affect the stability of non-VZV viruses and that rHA is an acceptable substitute for hydrolyzed gelatin in live virus vaccine stabilizers. This represents a significant advance because such replacement of gelatin avoids any potential safety concerns that might be raised by the fact that gelatin is derived from animals. Thus, it is feasible and desirable to include rHA in a stabilizer for M-M-R®II vaccine or in combination vaccines that include VZV and other viruses, such as M-M-R®II-VZV.

Figure 1A:
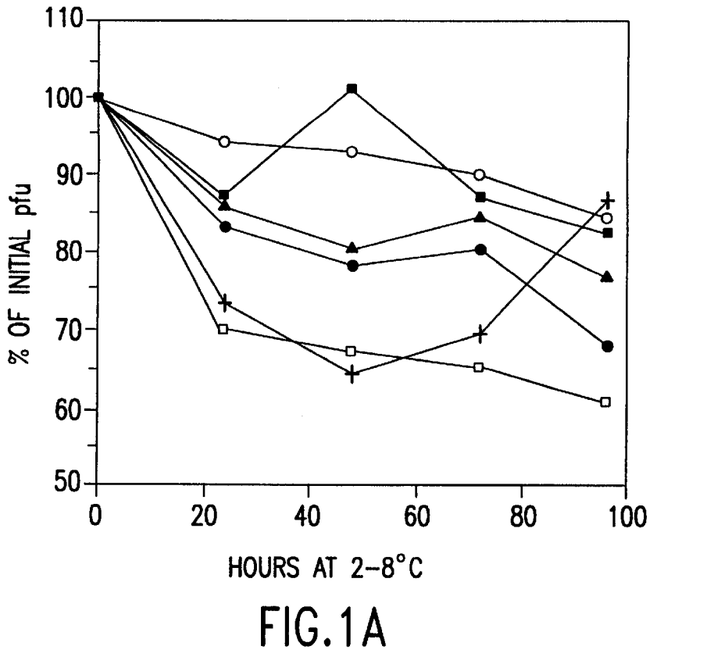
FIG. 1A shows the stability of measles virus at 2–8° C. in various stabilizers. ----□----=1x HSA; ----■----=1x rHA; ----●----=2x rHA; ----▲----=4x rHA; ----○----=0.5x rHA; ----|----=no albumin. See Example 3 for details.
Figure 1B:
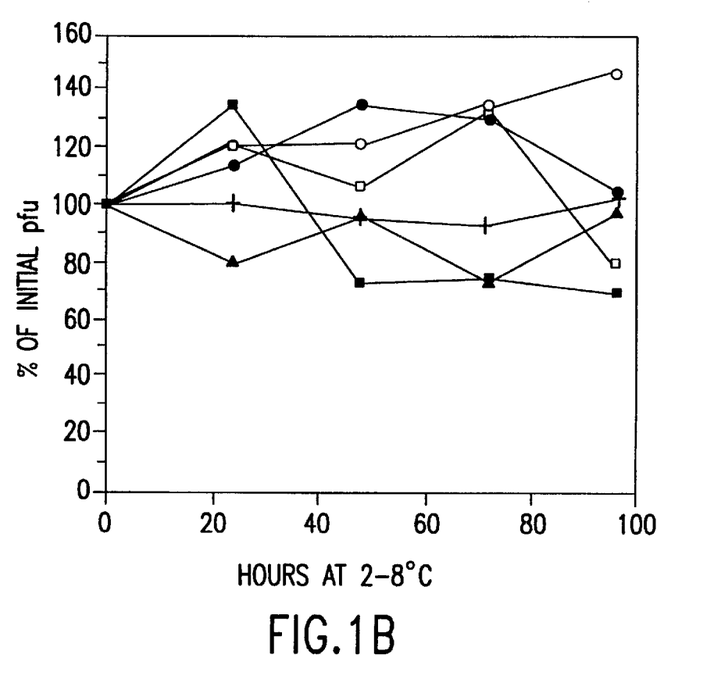
FIG. 1B shows the stability of rubella virus at 2–8° C. in various stabilizers. ----□----=1x HSA; ----■----=1x rHA; ----●----=2x rHA; ----▲----=4x rHA; ----○----=0.5x rHA; ----|----=no albumin. See Example 3 for details.

This conclusion is underscored by further studies, illustrated in FIGS. 1A and 1B, which demonstrated that the inclusion of rHA in tissue culture media does not adversely affect, and in some cases can improve, the stability of non-VZV viruses. FIGS. 1A and 1B represent the results of studies of the stability of measles and rubella virus in M-M-R®II incubated at 2–8° C. in tissue culture media containing either non-recombinant human serum albumin (HSA), rHA at various concentrations, or no albumin.

The compositions tested in FIG. 1A were as follows:

| 1× HSA | = | Medium 199 containing: |
|---|---|---|
| | | 50 µg/ml neomycin; |
| | | 2 mM L-glutamine; |
| | | 25% SPG (v/v); and |
| | | 0.25% HSA. |
| | | where SPG is SPGA (described earlier) without alubumin. |

-continued

| 1× rHA | = | Same as 1 × HSA except that 0.25% rHA was substituted for HSA |
| 2× rHA | = | Same as 1 × HSA except that 0.50% rHA was substituted for HSA |
| 4× rHA | = | Same as 1 × HSA except that 1.0% rHA was substituted for HSA |
| 0.5× rHA | = | Same as 1 × HSA except that 0.125% rHA was substituted for HSA |
| No albumin | = | Same as 1 × HSA except that HSA was omitted (and rHA was not added). |

The stabilizers tested in FIG. 1B were as follows:

| 1× HSA | = | 60% MEM containing: |
| | | 50 µg/ml neomycin; |
| | | 2 mM L-glutamine; |
| | | 25% SPG (v/v); and |
| | | 0.4% HSA |
| | | 40% sorbitol-gelatin where sorbitol-gelatin is 35.7 g/L sorbitol, 35.7 g/L hydrolyzed gelatin, and 0.1M sodium phosphate, in tissue culture medium. |
| 1× rHA | = | Same as 1 × HSA except that 0.4% rHA was substituted for HSA. Thus, the final rHA concentration was 0.24%. |
| 2× rHA | = | Same as 1 × HSA except that 0.8% rHA was substituted for HSA. Thus, the final rHA concentration was 0.48%. |
| 4× rHA | = | Same as 1 × HSA except that 1.6% rHA was substituted for HSA. Thus, the final rHA concentration was 0.96%. |
| 0.5× rHA | = | Same as 1 × HSA except that 0.2% rHA was substituted for HSA. Thus, the final rHA concentration was 0.12%. |
| No albumin | = | Same as 1 × HSA except that HSA was omitted (and rHA was not added). |

From the results shown in FIGS. 1A and 1B, several conclusions can be drawn:

For measles virus at 2–8° C., rHA at all concentrations tested within the range of 0.125% to 1.0% is more effective than HSA.

For rubella virus at 2–8° C., the scatter of points makes it difficult to draw firm conclusions, but it appears that rHA at concentrations ranging from 0.12% to 0.96% is at least as effective as HSA.

The above results demonstrate that for measles and rubella virus at 2–8° C., rHA is at least as effective as HSA, and, under some conditions, may be more effective. Similar data was generated under more accelerated conditions of incubation at 35° C.

In addition, one may conclude from these results that, over the range of concentrations 0.12% to 1.0%, the amount of rHA in a vaccine stabilizer does not seem to have a marked influence on the effectiveness of the stabilizer for liquid state stability of the viruses. In other words, if rHA is effective at 1.0%, it is also likely to be effective at 0.12%.

EXAMPLE 4
Recombinant Human Serum Albumin

Recombinant human serum albumin (rHA) was obtained from Centeon, Inc. The rHA had been prepared in *Saccharomyces cerivisiae* which had been recombined with the human gene for albumin together with a leader sequence which regulates the secretion of the recombinant protein into the fermentation medium. A semi-continuous method of fermentation is used. The fermentation media was centrifuged after incubation to separate the yeast cells from the centrate which contains rHA. The centrate was purified extensively by mulitple step chromatography to a purity where remaining yeast proteins are approximately 1 ppm (limit of detection). Then the product was concentrated by ultrafiltration to obtain solutions of up to 25% (w/v). The product is formulated with 0.16 mmol of octanoate per gram of rHA and 15 mg of Tween-80 per liter.

The above-described process for making rHA is meant to be illustrative only. rHA made by any recombinant process in yeast host cells may be used in the present invention. Such processes are well known in the art.

According to literature reports, aggregation of rHA has been observed in the lyophilized state and can cause problems for vaccine preparation (Constantino et al., 1995, Bio/Technol. 13:493–496). Therefore, the aggregation state of rHA in several vaccine formulations of the present invention was examined. After incubation of the formulations at 37° C. for 1 week or 4° C. for 2 months, no significant change in aggregate content was observed using analytical non-denaturing size exclusion HPLC (SEC-HPLC). In addition, conformational data collected from FTIR spectra suggest that the secondary structure of rHA was not changed after incubation in the lyophilized state.

TABLE 7

| Stabilizer | Storage conditions | % Aggregate | % Monomer |
|---|---|---|---|
| (rHA)OS | liquid, −70° C., control | 3.1 | 96.9 |
| | lyophilized, −70° C., control | 3.3 | 96.7 |
| | lyophilized, 37° C., 1 week | 3.7 | 96.3 |
| | lyophilized, 4° C., 1 month | 3.4 | 96.6 |
| | lyophilized, 4° C., 2 months | 3.6 | 96.4 |
| (rHA)OS33 | liquid, −70° C., control | 3.7 | 96.3 |
| | lyophilized, −70° C., control | 3.7 | 96.3 |
| | lyophilized, 37° C., 1 week | not tested | not tested |
| | lyophilized, 4° C., 1 month | 3.6 | 96.3 |
| | lyophilized, 4° C., 2 months | 3.7 | 96.3 |
| P(rHA)S in VARIVAX ® | liquid, −70° C., control | 2.7 | 97.3 |
| | lyophilized, −70° C., control | 2,7 | 97.3 |
| | lyophilized, 37° C., 1 week | 2.6 | 97.4 |
| | lyophilized, 4° C., 1 month | 2.6 | 97.3 |
| | lyophilized, 4° C., 2 months | 2.7 | 97.3 |
| P(rHA)S in MMRV | liquid, −70° C., control | 2.7 | 97.3 |
| | lyophilized, −70° C., control | 2.7 | 97.3 |
| | lyophilized, 37° C., 1 week | 2.8 | 97.2 |
| | lyophilized, 4° C., 1 month | 2.7 | 97.3 |
| | lyophilized, 4° C., 2 months | 2.7 | 97.3 |

The composition of (rHA)OS33 per liter is:

| | |
|---|---|
| rHA Solution, 25% w/v | 159 mL |
| Sorbitol | 84.2 g |
| Sucrose | 44.4 g |
| Tissue Culture Medium | balance. |

In the above-described stabilizer (rHA)OS33, the amount of sorbitol and sucrose can be varied. The amount of sorbitol can be from 20–90 g/l and the amount of sucrose can be from 2–70 g/l. The amount of rHA can vary from 0.1% to 10%.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties

What is claimed:

1. A live virus vaccine comprising:
   (a) live varicella zoster; and
   (b) recombinant human serum albumin (rHA) at a concentration of 0.1% to 10% (w/v) wherein the rHA has been made in yeast.

2. A live virus vaccine prepared by lyophilizing the vaccine of claim 1.

3. The vaccine of claim 2 wherein the yeast is *Saccharomyces cerevisiae*.

4. The vaccine of claim 1 wherein the rHA concentration is from 0.5% to 5%.

5. The vaccine of claim 1 wherein the rHA concentration is from 1% to 3%.

6. The vaccine of claim 1 further comprising measles, mumps, and rubella viruses.

7. The vaccine of claim 1 further comprising a sugar or sugar alcohol at 20–90 g/l; a mono- or dibasic alkali metal phosphate salt or mixture thereof at a total phosphate concentration of from 0.5 to 3 g/l; a glutamic acid alkali metal salt at 0.5 to 2 g/l; and a combination of sodium and potassium chloride providing a total chloride concentration of 4–10 g/l.

8. The vaccine of claim 1 further comprising, per liter:

| | |
|---|---|
| Potassium Chloride | 0.05–0.3 g |
| Potassium Phosphate Monobasic | 0.05–0.3 g |
| Sodium Chloride | 4–10 g |
| Sodium PhosphateDibasic | 0.5–2 g |
| Sodium L-glutamate or Potassium L-glutamate | 0.5–2 g |
| Sucrose, Sorbitol, Lactose, Glucose, Fructose, or Mannitol | 20–90 g. |

9. The vaccine of claim 8 comprising, per liter:

| | |
|---|---|
| Potassium Chloride | 0.16 g |
| Potassium Phosphate Monobasic | 0.16 g |
| Sodium Chloride | 6.4 g |
| Sodium PhosphateDibasic | 0.91 g |
| Sodium L-glutamate | 1.0 g |
| Sucrose | 50.0 g. |

10. The vaccine of claim 1 further comprising, per liter: sorbitol at 20–90 g/l; sucrose at 0–70 g/l; 1 M Sodium Phosphate, pH 6.2, at 65–85 mL; and Tissue Culture Medium.

11. The vaccine of claim 1 wherein the rHA concentration is 26.75 g/l and further comprising, per liter:

| | |
|---|---|
| Sorbitol | 56.8 g |
| 1M Sodium Phosphate, pH 6.2 | 75.0 ml |
| Tissue Culture Medium | balance. |

12. The vaccine of claim 1 wherein the rHA concentration is 39.75 g/l and further comprising, per liter:

| | |
|---|---|
| Sorbitol | 84.2 g |
| Sucrose | 44.4 g |
| Tissue Culture Medium | balance. |

13. The vaccine of claim 1 wherein the yeast is *Saccharomyces cerevisiae*.

14. A live virus vaccine comprising:

(a) live varicella zoster; and (b) Medium 199 containing:

rHA at a concentration of 0.1% to 10%;

50 $\mu$g/ml neomycin;

2 mM L-glutamine and;

25% SPG where SPG contains, on a per liter basis:

| | |
|---|---|
| Sucrose | 74.62 g |
| $KH_2PO_4$ | 0.52 g |
| $K_2HPO_4$ | 1.25 g |
| Potassium L-glutamate | 0.912 g | wherein the rHA has been made in yeast.

15. A method of preparing a live virus vaccine that comprises mixing live varicella zoster with a stabilizer comprising an aqueous solution of recombinant human serum albumin (rHA) at 1–100 g/l; a sugar or sugar alcohol at 20–90 g/l; a mono- or dibasic alkali metal phosphate salt or mixture thereof at a total phosphate concentration of from 0.5 to 3 g/l; a glutamic acid alkali metal salt at 0.5 to 2 g/l; and a combination of sodium and potassium chloride providing a total chloride concentration of 4–10 g/l wherein the rHA has been made in yeast.

16. The method of claim 15 wherein the ratio of live virus preparation to stabilizer is between 1:100 and 1:1 (v/v).

17. The method of claim 16 wherein the ratio of live virus preparation to stabilizer is 1:3 (v/v).

18. The method of claim 16 wherein the ratio of live virus preparation to stabilizer is 1:2 (v/v).

19. A method of harvesting varicella zoster virus for use in a live virus vaccine that includes the step of disrupting cells containing varicella zoster virus in the presence of a stabilizer comprising an aqueous solution of recombinant human serum albumin (rHA) at 1–100 g/l; a sugar or sugar alcohol at 20–90 g/l; a mono- or dibasic alkali metal phosphate salt or mixture thereof at a total phosphate concentration of from 0.5 to 3 g/l; a glutamic acid alkali metal salt at 0.5 to 2 g/l; and a combination of sodium and potassium chloride providing a total chloride concentration of 4–10 g/l wherein the rHA has been made in yeast.

* * * * *